US006293792B1

(12) United States Patent
Hanson

(10) Patent No.: US 6,293,792 B1
(45) Date of Patent: Sep. 25, 2001

(54) DENTAL SYRINGE TIP

(75) Inventor: Richard W. Hanson, Beaverton, OR (US)

(73) Assignee: DCI International, Inc., Newberg, OR (US)

( * ) Notice: Subject to any disclaimer, the term of this patent is extended or adjusted under 35 U.S.C. 154(b) by 0 days.

(21) Appl. No.: 09/556,041

(22) Filed: Apr. 21, 2000

(51) Int. Cl.[7] ............................................. A61C 17/00
(52) U.S. Cl. ................................................ 433/80; 433/127
(58) Field of Search ............................. 433/80, 126, 127, 433/128

(56) References Cited

U.S. PATENT DOCUMENTS

Re. 35,147 * 1/1996 Apap et al. .......................... 433/128
3,698,088 * 10/1972 Austin, Jr. .............................. 433/80
4,248,589 * 2/1981 Lewis ................................... 433/126
4,975,054 * 12/1990 Esrock .................................. 433/80
5,028,181 * 7/1991 Jenkins et al. ....................... 433/128
5,125,835 * 6/1992 Young .................................. 433/80

* cited by examiner

Primary Examiner—John J. Wilson
(74) Attorney, Agent, or Firm—TraskBritt, P.C.

(57) ABSTRACT

A quick-connect syringe tip for use with a dental handpiece. The syringe tip resists rotation about an axis through the connection end, allowing retraction of a cheek or lip without changing the orientation of a discharge fluid stream.

7 Claims, 1 Drawing Sheet

DENTAL SYRINGE TIP

BACKGROUND OF THE INVENTION

1. Field

This invention relates to hand held systems for discharging fluids. It is particularly directed to a quickly connectable nozzle which resists rotation, of particular benefit in a dental syringe tip.

2. State of the Art

Syringe tips used in dental practice typically connect to a handpiece having one or more valves to control flow of one or more fluids. A dental practitioner directs the controlled flow of fluids by aiming the discharge end of the syringe tip. Dental syringe tips generally have a bend between connection and discharge ends to provide ergonomic aiming of the dispensed fluids. They must be changed between patients to provide each new patient with a sterile tip. Quick-connect syringe tips and handle mechanisms, such as taught by U.S. Pat. No. 5,125,835, the disclosure of which is incorporated as though fully set forth herein, have been developed to speed the tip changing procedure.

A dental syringe tip may also find beneficial use as a retractor mechanism to move a patient's cheek or lip away from a site of operating interest. Currently available quick-connect syringe tips rotate under influence of the cheek or lip being retracted during the retraction procedure. The rotated tip is then typically aimed for discharge of fluids in an inconvenient direction. Correction of the tip orientation then typically requires a manual manipulation of the tip by the dental practitioner. Reorienting the tip causes an interruption, disrupting smooth flow of the operation. It is desirable to provide a quick-connect syringe tip that resists rotation during cheek or lip retraction.

SUMMARY OF THE INVENTION

The present invention provides a quick-connect dental syringe tip which resists rotation during a cheek or lip retraction procedure. An exemplary syringe tip may be used with a dental handpiece having a quick-connect device for tip attachment. A tip typically provides one or more conduits for fluids between a discharge end and a connection end The conduit at the discharge end may be oriented non linear with respect to the conduit at the connection end to provide aim of a discharge stream. An exemplary tip has retaining structure, associated with the connection end, adapted to interface in axial retaining relation with structure of a quick-connect mechanism of a dental handpiece. Anti-rotation structure, also associated with the connection end of a tip, resists a change in direction of a discharge stream when using the tip for a cheek or lip retraction procedure. The anti-rotation structure may be embodied as a first element, typically an indentation, located on the exterior of the connection end of a tip and shaped to engage in a structural interference with a cooperating second element of the dental handpiece. Alternatively, the first element (whether an indentation or other structural feature) may be shaped to engage in a structural interference with cooperating structure of the quick-connect mechanism. In certain tip configurations, both anti-rotation and retaining functions may be provided by a structural element located on the exterior of the connection end of a tip. In such configurations, the structural element may be shaped to form a structural interference with one or more elements of the quick-connect mechanism. In certain embodiments, the anti-rotation structure and the retaining structure may be formed by a plurality of indentations in the exterior of the connection end of a tip. A currently preferred tip configuration includes anti-rotation structure adapted to resist rotation of the tip from a pre-positioned orientation. That is, the rotational orientation may be set in any of a plurality of discrete rotation orientations circumferentially spaced apart about the connection end.

These features, advantages, and alternative aspects of the present invention will be apparent to those skilled in the art from a consideration of the following detailed description taken in combination with the accompanying drawings.

BRIEF DESCRIPTION OF THE DRAWINGS

In the drawings, which illustrate what is currently regarded as the best mode for carrying out the invention.

DETAILED DESCRIPTION OF THE ILLUSTRATED EMBODIMENT

Figure 1:
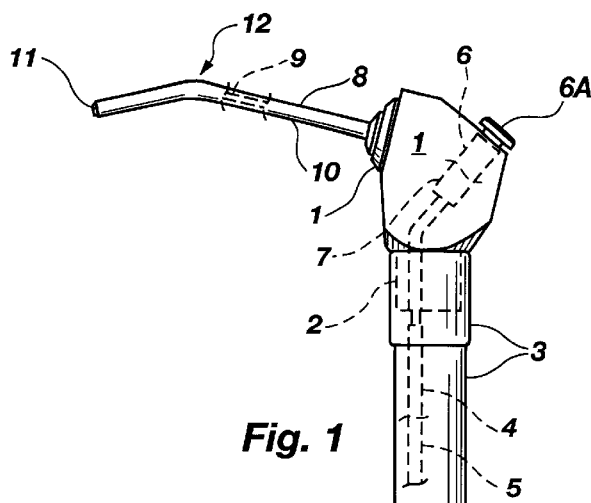
FIG. 1 is a side view in elevation of an exemplary dental syringe provided with a syringe tip according to the present invention.
Figure 2:
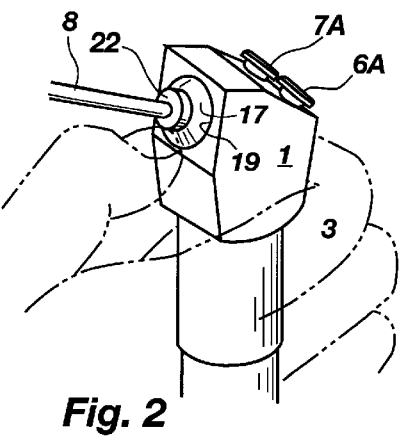
FIG. 2 is a fragmentary perspective view of the syringe of FIG. 1 during removal of the tip.

A commercially available syringe head 1 having a threaded boss 2 for detachable engagement with a tubular handle 3 is illustrated in FIGS. 1 and 2. The syringe head 1 is supplied by pressurized water and air lines 4 and 5. Finger operated water and air valve assemblies 6 and 7 are suitably secured within bores in the syringe head 1 with each valve assembly being equipped with a corresponding push button control 6A and 7A. Passages in the head 1 communicate lines 4 and 5 with the valve assemblies 6 and 7. Other passages in head 1 serve to communicate the valve assemblies 6 and 7 with an exemplary syringe tip 8.

A tip 8 may be provided with inner and outer concentric conduits 9 and 10 adapted to discharge in either a singly or combined manner at a discharge end 11. Provision of a single fluid conduit is also within contemplation in a tip 8. It is to be understood that a plurality of fluid conduits, in excess of the illustrated two, may additionally be included in a tip 8. Tips 8 are typically formed of metal, especially from stainless steels, to provide long life and allow multiple sterilization cycles. A bend, illustrated generally at 12, may be included to provide an ergonomic discharge direction of end 11 relative to head 1.

FIG. 2 illustrates the removal of an installed tip 8 by pressing quick-release device 17 into receiving bore 19 in head 1. Any other method of actuation of various quick-release mechanisms is workable with the instant syringe tip 8.

Figure 3:
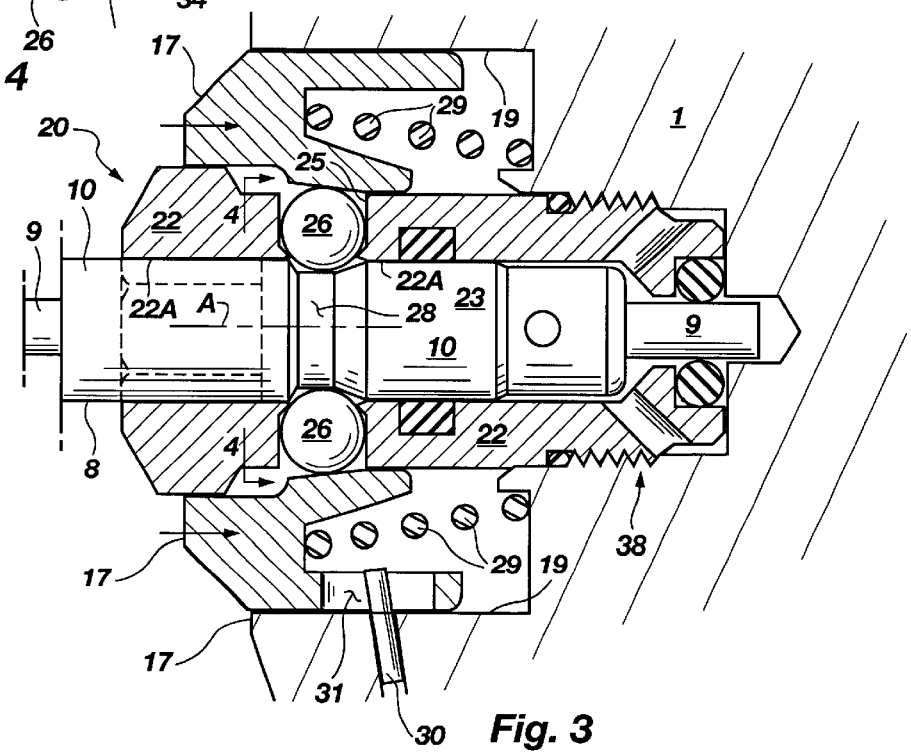
FIG. 3 is a vertical medial sectional view of a tip quick-connect mechanism assembly housed within a syringe head.

The illustrated quick-release mechanism of FIGS. 2 and 3 is exemplary only, and may be replaced by any other form of quick release mechanism which performs the desired attachment function. A quick release mechanism for use with the instant invention must merely provide a convenient attachment of the tip 8 to the head 1. Structure carried by either head 1 or within the release mechanism may provide a resistance to rotation of the tip 8 about an axis A (see FIG. 3). Axis A is considered to be generally parallel to a conduit in tip 8.

As one example, a quick-release mechanism within contemplation provides multiple fingers configured to interface with an axially oriented retaining structure carried by a tip 8, such as a groove, divot, or journal. The multiple fingers may be configured to provide a resistance to rotation by tightly gripping structure of the tip 8 to provide a frictional resistance to rotation. The fingers may take many shapes, non exclusively including ovals, balls, bricks, disks, half moons, and other geometric shapes. Of course, the fingers may also be shaped in part to interface with receiving structure carried by a connection end of the tip 8, thereby providing a structural interference providing resistance to rotation of tip 8.

As a further example, a tip 8 may be provided one or more slots in which to slidingly receive anti-rotation structure carried by a quick-connect system or head 1. The slot may provide a structural interference against rotation of the tip 8 about its connection end. A plurality of substantially fixed rotation orientations of a tip 8 may be provided in such a system, depending upon orientation of a tip during insertion in a head 1.

FIG. 3 illustrates additional structural details of one quick-connect mechanism to retain a tip 8 to a head 1. The illustrated mechanism is a ball actuated quick-connect mechanism, generally indicated at 20. Retaining collar 22 receives connection end 23 of tip 8 in bore 22A. Retaining collar 22 is provided with circumferentially spaced apart slots 25 in which to receive balls 26. Slots 25 provide for radial translation of balls 26 about axis A. Balls 26 are thereby arranged to cooperate with axial retaining structure, such as groove 28, carried by connection end 23, to axially retain a tip 8 to a head 1. When released, quick-release device 17 is shaped to urge balls 26 radially inward into groove 28 of an inserted tip 8. When depressed into bore 19, device 17 allows balls 26 to travel radially outward, and thereby axially release a tip 8. A spring element, illustrated as coil spring 29, may advantageously be included to urge device 17 into a tip-retaining position. Device 17 is substantially restrained from rotation and to translation between a tip release position and a tip retaining position by pin 30 captured within slot 31.

Figure 4:
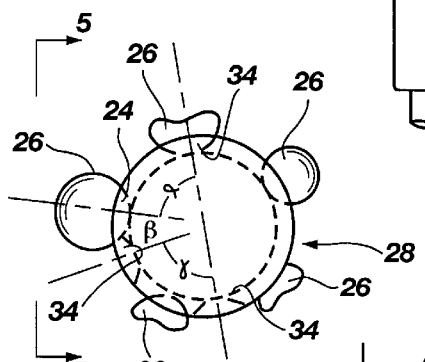
FIG. 4 is a vertical sectional view of a portion of an exemplary syringe tip, taken along section 4—4 of FIG. 3 and looking in the direction of the arrows.
Figure 5:
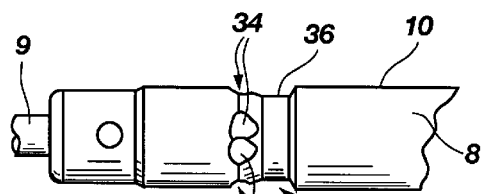
FIG. 5 is a horizontal view of the connection end of the syringe tip of FIG. 4, indicated by section 5—5 and looking in the direction of the arrows.

Axial retaining structure such as groove 28 may have many configurations and shapes other than the configuration illustrated in FIG. 3. Any structure carried by a tip 8 and functioning cooperatively with structure of a quick-release mechanism to axially retain a tip 8 to a head 1 is workable. FIGS. 4 and 5 illustrate an alternate configuration of groove 28. Axial retaining structure may alternately include one or more circumferentially discrete indentations or features in tip 8 which receive(s) quick-release structure in a structural interference against axial separation of tip 8 from head 1. Such an alternate configuration would simultaneously provide resistance to rotation of a tip 8 about axis A.

FIGS. 4 and 5 also present one configuration of anti-rotation structure illustrated as indentations 34. Indentations 34 are formed, in part, in the surface 36 of groove 28. Illustrated indentations 34 are adapted to fit to the balls 26, forming a structural interference against rotation of a tip 8 about axis A. In an installed position of a tip 8, selected balls 26 are maintained in contact with indentations 34 by device 17. Balls 26 are restrained from rotation about axis A by a circumferential constraint supplied by grooves 25 in collar 22. Collar 22 is restrained from rotation about axis A by its connection to head 1, including threaded interface 38. Accordingly, an installed tip 8 resists rotation.

FIG. 4 illustrates a quick-connect system having five balls 26. Any number of balls may be used, from one to perhaps 20 or more. The upper limit is perhaps best determined by manufacturing considerations. In FIG. 4, a currently preferred embodiment, the four indentations 34 are illustrated as being spaced apart around the circumference of groove 28 such that two balls 26 may be received in two indentations 34 at the same time. Indentations 34 are spaced apart by angles $\alpha$, $\beta$, and $\gamma$. In the illustrated 5-ball embodiment, $\alpha$ and $\gamma$ are about 72 degrees, and $\beta$ is about 36 degrees. It has been found that in such a 5-ball system, it is advantageous to provide for the capture of at least two of the five balls to form a reliable retaining function with a head 1. Device 17 has been found to receive too much support from the four non-captured balls 26 to reliably seat a single captured ball 26 in an indentation 34 in a five-ball quick-release mechanism.

An advantage provided by the spacing apart of the indentations 34 illustrated in FIGS. 4 and 5 is the ability to resist rotation of a tip 8 from one of a plurality of discrete orientations. The illustrated configuration provides ten individual tip orientations, circumferentially spaced apart, in which the indentations 34 align with and capture a pair of balls 26.

Within the context of this disclosure, resisting rotation of a tip 8 about a conduit at a connection end means that the interface between a tip 8 and the retaining system provides sufficient resistance to rotation to be able reliably to retract a cheek or lip using the tip 8, installed in a head 1, without causing rotation of the tip. Such resistance to rotation therefore spans between absolute prevention of rotation of a tip 8 and resistance to rotation which may be overcome by finger pressure. A workable embodiment of the invention may be oriented to a discrete rotation resisting position by rotating a fully installed tip 8 using finger pressure. In the discrete rotation resisting position, the tip may be used as a retraction aid without changing its discharge direction.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental syringe tip comprising:

a conduit for fluids between a discharge end and a connection end of said tip;

retaining structure, comprising a groove in an exterior surface of the connection end, adapted to interface in retaining relation with a plurality of retaining elements disposed for substantially radial translation in a quick-connect device of a dental handpiece to prevent inadvertent disconnection of the tip from the handpiece;

fluid sealing structure adapted to form a fluid tight seal between said connection end and structure carried by said handpiece when fluid is applied to said conduit; and anti-rotation structure, associated with the connection end, configured and arranged cooperatively with structure carried by said handpiece to resist rotation of the tip about the conduit at the connection end, wherein the anti-rotation structure comprises a plurality of indentations in a surface of said groove, said indentations being shaped and spaced apart circumferentially to accommodate engagement with a plurality of retaining elements of said quick-connect device.

2. A dental syringe tip comprising:

a conduit for fluids between a discharge end and a connection end of said tip;

retaining structure, associated with the connection end, adapted to interface in retaining relation with a plurality of retaining elements disposed for substantially radial translation in a quick-connect device of a dental handpiece to prevent inadvertent disconnection of the tip from the handpiece;

fluid sealing structure adapted to form a fluid tight seal between said connection end and structure carried by said handpiece when fluid is applied to said conduit; and anti-rotation structure, associated with the connection end, configured and arranged cooperatively with structure carried by said handpiece to resist rotation of the tip about the conduit at the connection end, wherein:

the retaining structure comprises a radial groove about the perimeter and spaced from an extreme end portion of the syringe tip connection end, and the anti-rotation structure comprises a plurality of indentations in a surface of the groove, the indentations being shaped to accommodate engaging structure of the quick-connect device.

3. The apparatus of claim 2, wherein said plurality of indentations are adapted to receive retaining ball elements of the quick-connect device to resist rotation of said tip at an orientation selected from a plurality of discrete rotated positions circumferentially spaced apart about said connection end.

4. The apparatus of claim 3, wherein the indentations are spaced apart around the circumference of the connection end whereby to interface with less than the total number of retaining ball elements active in the quick-connect device.

5. In a syringe tip having a connection end and a discharge end, a fluid sealing surface disposed at said connection end, and with a radial groove disposed circumferentially at said connection end for attachment to a dental handpiece by way of a ball actuated quick-connect device, the improvement comprising an indentation formed in a surface of said groove, said indentation being adapted to receive a ball element of said device in engagement whereby to resist rotation of said tip about an axis through said connection end.

6. The apparatus according to claim 5, further comprising a plurality of indentations formed in said groove, said indentations being spaced apart in a circumferential direction of said groove whereby in combination to receive a plurality of ball elements of said device for purpose of resisting rotation of said tip about said axis thereby to preferentially maintain said tip at an orientation selected from a plurality of discrete rotated positions circumferentially spaced apart about said connection end.

7. The apparatus of claim 6, the number and spacing of said indentations being arranged to receive less than the total number of retaining ball elements active in said device.

* * * * *

UNITED STATES PATENT AND TRADEMARK OFFICE
CERTIFICATE OF CORRECTION

PATENT NO. : 6,293,792 B1
DATED : September 25, 2001
INVENTOR(S) : Richard W. Hanson It is certified that error appears in the above-identified patent and that said Letters Patent is hereby corrected as shown below:

Column 1,
Line 43, after "end" and before "The" insert -- . --
Line 44, change "non linear" to -- non-linearly --
Line 47, after "structure" delete ","
Lines 49-50, change "Anti-rotation" to -- An anti-rotation --
Line 59, after "cooperating" and before "structure" insert -- a --

Column 2,
Line 2, after "includes" and before "anti-rotation" insert -- an --
Lines 41, 43, 55, 58, 66 and 67, before "head" insert -- syringe --
Line 42, before "lines" insert -- with --
Line 42, after "5" insert -- and --
Lines 45, 48, 51, 56 and 66, before "tip" insert -- syringe --
Line 51, change "Tips" to -- Syringe tips --
Line 55, before "end" insert -- discharge --
Lines 63 and 64, change "quick release" to -- quick-release --

Column 3,
Lines 1, 3, 6, 9, 14, 16, 17, 20, 22, 26, 29, 35, 37 and 39, before "tip" insert -- syringe --
Line 17, after "provided" insert -- with --
Lines 19, 24, 26 and 35, before "head" insert -- syringe --
Line 37, before "bore" insert -- receiving --
Lines 38 and 41, before "device" insert -- quick-release --
Line 41, change "Device" to -- Quick-release device --
Lines 45 and 51, "Axial" to -- An axial --
Lines 47, 49, 53, 54, 56, 61 and 62, before "tip" insert -- syringe --
Line 48, after "with" insert -- a --
Line 49, after "mechanism" insert -- 17 --
Lines 49 and 54, before "head" insert -- syringe --
Line 63, before "device" insert -- quick-release --
Line 65, change "25" to -- 28 --
Line 65, "collar" insert -- retaining --
Line 66, "Collar" to -- Retaining collar --

UNITED STATES PATENT AND TRADEMARK OFFICE
CERTIFICATE OF CORRECTION

PATENT NO. : 6,293,792 B1
DATED : September 25, 2001
INVENTOR(S) : Richard W. Hanson It is certified that error appears in the above-identified patent and that said Letters Patent is hereby corrected as shown below:

<u>Column 4,</u>
Lines 1, 15 and 31, before "head" insert -- syringe --
Lines 2, 22, 28, 29, 31, 32, 34, 37 and 38, before "tip" insert -- syringe --
Line 5, change "20" to -- 20 --
Line 15, change "Device" to -- Quick-release device --
Line 32, after "rotation" insert -- , --
Line 33, after "therefore" insert -- , --

Signed and Sealed this

Twentieth Day of May, 2003

JAMES E. ROGAN
*Director of the United States Patent and Trademark Office*